United States Patent [19]
Lawson et al.

[11] Patent Number: 6,008,416
[45] Date of Patent: Dec. 28, 1999

[54] PRODUCTION OF MIBK USING CATALYTIC DISTILLATION TECHNOLOGY

[75] Inventors: Keith Henry Lawson; Bongani Nkosi, both of Sasolburg, South Africa

[73] Assignee: Catalytic Distillation Technologies, Pasadena, Tex.

[21] Appl. No.: 09/098,238

[22] Filed: Jun. 16, 1998

[30] Foreign Application Priority Data

Jun. 18, 1997 [ZA] South Africa .............. 97/5383

[51] Int. Cl.$^6$ .................................................. C07C 45/45
[52] U.S. Cl. ............................................................ 568/396
[58] Field of Search ............................................. 568/396

[56] References Cited

U.S. PATENT DOCUMENTS

| | | | |
|---|---|---|---|
| 3,666,816 | 5/1972 | Takagi et al. ........................ | 568/396 |
| 3,953,517 | 4/1976 | Schmitt et al. ...................... | 568/396 |
| 4,306,068 | 12/1981 | Smith, Jr. ........................... | 546/184 |
| 4,332,968 | 6/1982 | Smith, Jr. ........................... | 564/278 |
| 5,059,724 | 10/1991 | Chen et al. ......................... | 568/396 |
| 5,149,881 | 9/1992 | Ushikubo et al. ................... | 568/396 |
| 5,684,207 | 11/1997 | Chen et al. ......................... | 568/396 |

*Primary Examiner*—Elli Peselev
*Attorney, Agent, or Firm*—Kenneth H. Johnson

[57] ABSTRACT

A process for the production of methyl isobutyl ketone from acetone and hydrogen utilizing a catalytic distillation column reactor. The reactions take place in a reaction zone with the reaction products being removed from the reaction zone and unreacted acetone being refluxed. The equilibrium is thus continuously disturbed allowing for greater than equilibrium conversion of acetone.

26 Claims, 1 Drawing Sheet

PRODUCTION OF MIBK USING CATALYTIC DISTILLATION TECHNOLOGY

BACKGROUND OF THE INVENTION

Field of the Invention

This invention relates to the production of methyl isobutyl ketone, an important industrial solvent. The invention relates in particular to a process for producing methyl isobutyl ketone. According to the invention, there is provided a process for producing methyl isobutyl ketone, which process comprises introducing acetone and hydrogen into a treatment zone; subjecting the acetone to catalytic distillation in the treatment zone in the presence of the hydrogen to convert at least some of the acetone to methyl isobutyl ketone; and withdrawing methyl isobutyl ketone from the treatment zone.

SUMMARY OF THE INVENTION

Catalytic distillation involves effecting chemical reactions simultaneously with or in combination with distillation in a single treatment zone. In the present invention, the following reactions take place in the treatment zone to produce methyl isobutyl ketone (MIBK):

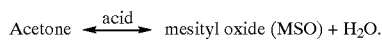

(1)

hydrogenation:

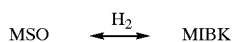

(2)

The dimerization/dehydration reaction, (1) is extremely equilibrium limited under conventional operating conditions.

The treatment zone thus comprises (1) at least one reaction zone in which the dimerization/dehydration reaction of the acetone to convert it to mesityl oxide, i.e. reaction (1), and the hydrogenation reaction to convert the mesityl oxide to the methyl isobutyl ketone, i.e. reaction (2), take place in the presence of a catalyst and at least one distillation zone adjacent the reaction zone in which distillation of the reaction products from the reaction zone and/or unreacted reactants takes place.

The catalyst is preferably bifunctional. Thus, the catalyst may promote or catalyze the dimerization/dehydration reaction, i.e., reaction (1) and the hydrogenation reaction, i.e. reaction (2). The dimerization/dehydration function of the catalyst (reaction (1)), which is acidic in nature, can be provided by an ion exchange resin such as a divinyl benzene based cation exchange resin, a styrene based cation exchange resin, an Amberlyst (trademark) resin, or the like; a zeolite, or alumina, preferably a cation exchange resin. As resins have temperature limitations the temperature conditions in the reaction zone should not exceed about 135° C. The hydrogenation function can be provided by metal preferably a metal of Group VIII and IB of the Periodic Table of Elements, such as nickel, palladium or copper.

The treatment zone will typically be provided by a column. The catalyst may be in particulate form and may be arranged in the form of a packed bed located in the reaction zone. The catalyst bed may be located above the point or level at which the acetone enters the column. Suitable packed distillation media, e.g. Raschig rings, or distillation apparatus or equipment, are then provided in the column below and/or above the catalyst bed, i.e. in the distillation zone(s).

The temperature and pressure inside the column are selected such that the acetone is at its boiling point at the column pressure. In other words, the temperature inside the column is controlled by means of pressure. The variation of the boiling point of acetone with pressure can be obtained from known sources such as simulation packages, e.g. the simulation package available under the trademark PRO II from Simulation Sciences, Inc. Preferably temperature conditions in the column are from 50° C.–160° C., more preferably 100° C.–135° C. Under these temperature conditions the pressure required to maintain the acetone at its boiling point does not exceed 15 bars.

The introduction of the hydrogen into the column is preferably at a lower level than the acetone but above the reboiler.

The methyl isobutyl ketone, any other by-products and condensed acetone may pass to the bottom of the reaction zone and reboiling these components in a reboiling stage located at the bottom of the column or reaction zone. The methyl isobutyl ketone and any other by-products, which have higher boiling points than acetone and are thus not significantly vaporized by the reboiling, may be removed as a product fraction or stream.

Any unreacted vaporized acetone may be withdrawn from the top of the column, condensed, and returned as a reflux to the column, at or above the catalyst bed.

In one embodiment of the invention the process is a continuous process with the introduction of the acetone being into the bottom of the column immediately above the reboiling stage and with the product fraction or stream being withdrawn continuously from the reboiling stage.

However, in another embodiment of the invention the process may be a batch one with the introduction of the acetone initially being effected into the reboiling stage. The process may then be terminated when a desired product specification is achieved in the reboiling stage, whereafter the methyl isobutyl ketone-containing product fraction is withdrawn from the reboiling stage.

DESCRIPTION OF THE PREFERRED EMBODIMENT

The invention will now be described by way of example with reference to the accompanying diagrammatic drawings and non-limiting examples set out hereunder.

Figure 1:
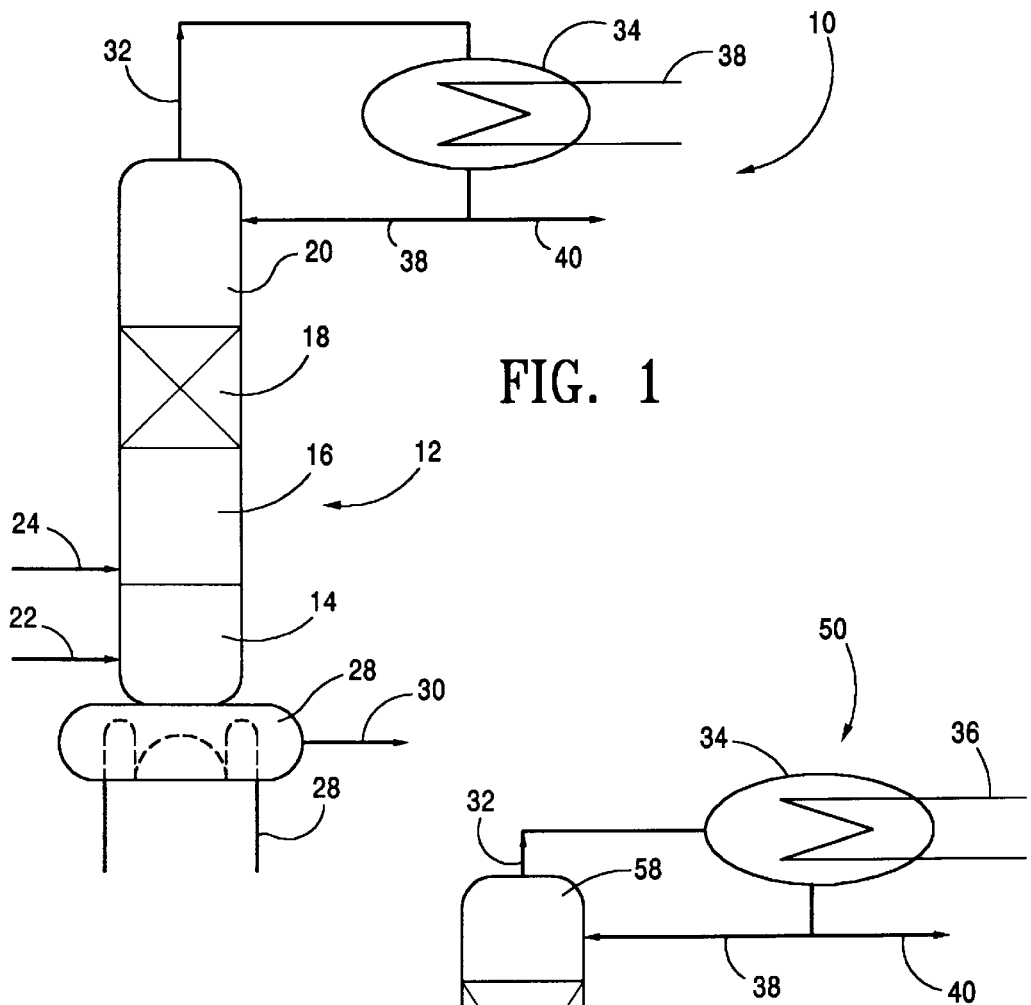
FIG. 1 shows schematically and in simplified flow diagram form a process according to one embodiment of the invention for producing methyl isobutyl ketone.

Referring to FIG. 1, reference numeral 10 generally indicates a process according to one embodiment of the invention for producing methyl isobutyl ketone.

The process 10 includes a catalytic distillation column 12 having four zones 14, 16, 18 and 20 therein, with the zone 14 being located lowermost and the zone 20 being located uppermost. The zones 14, 16, and 20 are distillation zones and are filled with distillation packing, such as Raschig rings. The zone 18 is a reaction zone and contains a packed catalyst bed. The catalyst in the bed 18 is in particulate form and is a combination or mixture of a particulate catalyst component having a dimerization/dehydration function such as Amberlyst resin, zeolites or alumina and a particulate catalyst component having a hydrogenation function such as nickel, palladium or copper.

An acetone feed line 24 leads into the zone 16 while a hydrogen feed line 22 leads into the zone 14.

A reboiler 26 is located at the lower end of the column 12 and is fitted with suitable heating means 28, such as a steam heating coil or electrical heating element, with a product withdrawal line 30 leading from the reboiler 26.

A vapor withdrawal line 32 leads from the top of the column 12 to a condenser 34 provided with suitable cooling or condensing means 36 such as a cooling water supply with a return or reflux line 38 leading back into the zone 20 of the column 12. A hydrogen withdrawal line 40 leads from the reflux line 38 for withdrawing any excess hydrogen through a back pressure regulator (not shown) fitted in the line 40.

It is to be appreciated that instead of the catalyst bed being located in the zone 18 it can be located in another zone of the column 12 provided that the acetone feed line 24 and the hydrogen feed line 22 are located below the catalyst bed.

In use liquid acetone is fed into the zone 16 of the column 12 through the acetone feed line 24. Simultaneously, hydrogen gas is introduced into the zone 16 of the column 14 through the hydrogen feed line 22.

The temperature inside the column 12 is controlled by means of pressure. The pressure and temperature conditions are selected such that the acetone is at its boiling point under the pressure conditions selected with the variation for the boiling point of acetone with pressure being obtainable from simulation package such as that available under the trademark PRO II from Simulation Sciences Inc. Thus, the temperature in the distillation column 12 can be maintained in the region of 100° C.–135° C. with the pressure than being matched to keep the acetone at its boiling point. Naturally, the reboiler 26 serves to vaporize the incoming acetone and to maintain it in vaporized state.

The gaseous hydrogen and the vaporized acetone thus move up the column 12 and react within the catalyst bed in the reaction zone 18. Mesityl oxide (MSO) is initially formed in accordance with reaction (1) hereinbefore described. The mesityl oxide is then subsequently hydrogenated to methyl isobutyl ketone (MIBK) in accordance with reaction (2) as hereinbefore described.

The methyl isobutyl ketone and any other by-products which are formed have higher boiling points than the acetone feed and therefore drop into the reboiler 26 from where they are removed along the product withdrawal line 30.

Unreacted acetone is refluxed at the top of the column 12 by being withdrawn along the flow line 32, condensed in the condenser 34 and returned to the top of the column along the flow line 38. No light boiling components are formed in reactions (1), (2), and (3), and thus there are no overhead products which are withdrawn from the column 12. In other words, the column 12 is operated under total reflux. Any unreacted hydrogen is withdrawn along the flow line 40.

The methyl isobutyl ketone product is thus formed in a single step using a single catalytic distillation column 12.

If necessary, i.e. depending on the selectivity of the catalyst used, any by-products formed may be separated from the methyl isobutyl ketone in another downstream distillation column (not shown) into which the flow line 30 leads.

Figure 2:
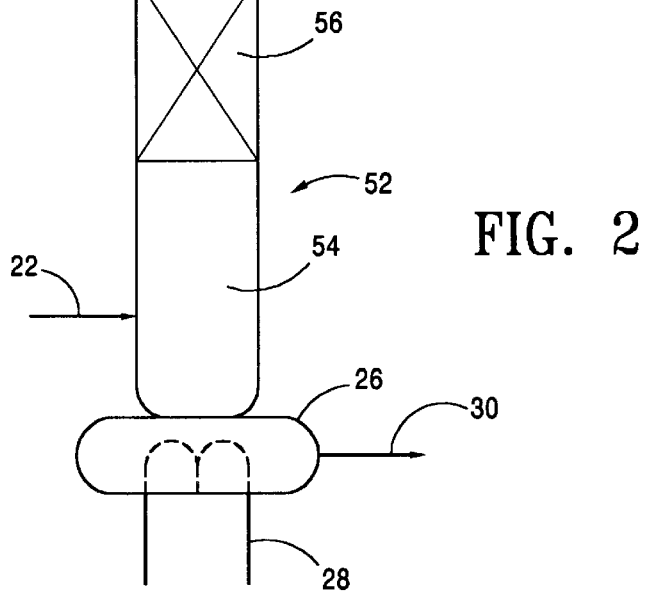
FIG. 2 shows schematically and in simplified flow diagram form a process according to another embodiment of the invention for producing methyl isobutyl ketone.

Referring to FIG. 2, reference number 50 generally indicates a process according to another embodiment of the invention for producing methyl isobutyl ketone.

Parts of the process 50 which are the same or similar to those of the process 10 hereinbefore described with reference to FIG. 1 are indicated with the same reference numerals.

The process 50 includes a column 52. The column 52 is similar to the column 12 but only has three zones 54, 56, and 58, with the zone 54 being located lowermost and the zone 58 being located uppermost. Distillation media such as Raschig rings are placed into the distillation zones 54, 58, while the catalyst bed is provided in the reaction zone 56. The hydrogen feed line 22 leads into the zone 54 in the lower part of this section.

The process 50 is a batch process and no acetone feed line leads into the column 52. However, a batch of acetone is initially introduced into the reboiler 26.

The reboiler 26 is electrically heated so that the heating means 28 is in the form of an electrical heating element.

In use, acetone which has vaporized in the reboiler 26 and hydrogen gas move upwardly through the catalyst bed in the zone 56. Unreacted acetone exits through the flow line 32, is condensed in the condenser 34 and is returned to the top of the column through the flow line 38. Unreacted hydrogen is withdrawn along the flow line 40.

The higher boiling methyl isobutyl ketone product which is formed and any other side products drop into the reboiler 26. The contents of the reboiler 26 are periodically analyzed. Since the pressure conditions inside the column are tailored such that they favor the boiling of acetone, the higher boiling products will be unable to boil in the reboiler and move up the column 52. Only acetone present in the reboiler 26 will boil and be vaporized and thus move up the column 52. Thus, more and more methyl isobutyl ketone and other side products accumulate in the reboiler 26 until no more acetone is available for reaction. When all available acetone has been used, there will be no component passing along the flow line 32 so that the condenser duty drops to zero at which point the reaction is terminated and the methyl isobutyl ketone product withdrawn along the flow line 30.

To show that the acetone dimerization/dehydration reaction, i.e. reaction (1) is extremely equilibrium limited under particular reaction conditions and would thus potentially benefit from catalytic distillation technology. Example 1 was conducted as follows:

EXAMPLE 1

The acetone dimerization/dehydration reaction (reaction (1) was performed in a batch autoclave over 48 hours so as to obtain conversion data close to the equilibrium value. 100 ml of acetone and 10 ml of a particulate 0.05% Pd/Amberlyst Rhom & Haas 15 catalyst were charged into the autoclave or reactor. The reactor was then purged twice with nitrogen prior to pressurizing it to 5 bars with nitrogen. The reactor was subsequently heated to 110° C. at a stirrer speed of 200 rpm for 48 hours. After cooling, the contents of the reactor were analyzed by gas chromatography (GC) and the results obtained from this run are given in Table 1.

As is evident from Table 1 the conversion of acetone is below 10% indicating that the acetone dimerization reaction is extremely equilibrium limited under the given reaction conditions and could benefit from catalytic distillation technology.

TABLE 1

| Acetone Conversion % | Name of Product | Selectivity % |
|---|---|---|
| 7.3 | MSO + Isomer | 82.31 |
|  | Others | 17.69 |

It was unexpectedly found that catalytic distillation has the advantage of increasing the conversion of the equilibrium limited acetone dimerization reaction of Example 1. For this, in Example 2, a batch-type catalytic distillation column was used substantially in accordance with FIG. 3 but having no hydrogen feed.

EXAMPLE 2

100 ml of a particulate 0.05% Pd/Amberlyst 15 catalyst was packed into the reaction zone 56 of the batch distillation column 52 and the remaining zones or sections 54 and 58 filled with 6 mm Raschig ring distillation packing. 1 l of acetone was charged into the reboiler of the column. The column was then pressurized to 5 bars using nitrogen. Heating of the reboiler was commenced and samples from the reboiler were taken periodically for GC analysis.

The data obtained from the run are presented below in Table 2. Much higher conversions are obtained when using catalytic distillation than were obtained when using a conventional batch reactor under similar reaction conditions as in Example 1. The results of this example clearly demonstrate that catalytic distillation technology has the advantage of increasing the conversion of equilibrium limited acetone dimerization reaction.

TABLE 2

|  |  | % Selectivity to |  | Temperature° C. |  |
|---|---|---|---|---|---|
| Time (hrs) | Acetone Conv % | MSO + Isomer | Others | Reaction Zone 56 | Reboiler 26 |
| 5 | 1.57 | 83.35 | 12.90 | 127.7 | 127.9 |
| 9 | 2.09 | 85.65 | 14.36 | 127.6 | 127.5 |
| 19 | 3.85 | 80.78 | 19.22 | 126.9 | 128.5 |
| 23 | 7.27 | 77.09 | 22.91 | 125.2 | 131.0 |
| 27 | 13.40 | 76.34 | 23.65 | 125.7 | 132.2 |
| 31 | 24.20 | 75.80 | 24.20 | 126.4 | 134.6 |
| 35 | 35.30 | 75.10 | 24.90 | 126.2 | 137.6 |
| 39 | 44.60 | 74.85 | 25.15 | 125.7 | 143.0 |
| 43 | 48.20 | 74.69 | 25.21 | 122.7 | 165.6 |
| 48 | 89.50 | 71.80 | 28.20 | 120.1 | 170.0 |

In Example 3, Example 1 was repeated except that hydrogen was used instead of nitrogen to pressurize the autoclave.

EXAMPLE 3

The reaction conditions were thus the same as those described in Example 1. However, hydrogen was used in place of nitrogen to pressurize the autoclave to 5 bars over 48 hours.

The results from this run are given in Table 3. The acetone conversion is much higher when hydrogen is used in place of nitrogen since the mesityl oxide is hydrogenated to methyl isobutyl ketone which assists in pushing the equilibrium towards the product or methyl isobutyl ketone side. The acetone conversion is, however, still lower than when catalytic distillation technology is used in the absence of hydrogen (Table 2). Additionally, there are still a lot of other products being formed even in the presence of hydrogen. These other products are by-products from further reactions to MSO such as phorone, isophorone, mesitylene, etc.

TABLE 3

| Acetone Conversion % | Name of Product | Selectivity % |
|---|---|---|
| 25.56 | MSO + Isomer | 19.25 |
|  | Others | 18.93 |
|  | MIBK | 61.19 |

Thereafter in Example 4, Example 2 was repeated except that a hydrogen feed was used, i.e., hydrogen was used to pressurize the column.

EXAMPLE 4

The reaction was performed in the same batch catalytic distillation column as used in Example 2, however, with hydrogen being used to pressurize the column. The hydrogen was passed over the catalyst or reaction zone at a flow rate of 7 normal liters per hour. The results are given in Table 4. These results show that catalytic distillation enhances conversion of acetone. However, not all of the mesityl oxide formed is hydrogenated to methyl isobutyl ketone due to the low hydrogen flow rates used under the low pressure conditions (5 bars) used in this run.

TABLE 4

|  |  | % Selectivity to |  |  | Temperature° C. |  |
|---|---|---|---|---|---|---|
| Time (hrs) | Acetone Conv % | MSO + Isomer | MIBK | Others | Reaction Zone 56 | Reboiler 26 |
| 4 | 13.20 | 75.00 | 15.00 | 6.82 | 124.9 | 129.7 |
| 8 | 13.83 | 61.94 | 22.43 | 14.33 | 127.6 | 131.5 |
| 12 | 19.85 | 56.83 | 22.82 | 17.93 | 128.3 | 134.7 |
| 16 | 25.48 | 58.35 | 23.23 | 19.90 | 127.5 | 139.0 |
| 20 | 35.54 | 58.02 | 27.46 | 16.59 | 125.5 | 145.6 |
| 24 | 78.22 | 47.69 | 33.02 | 16.83 | 125.9 | 157.9 |

In Example 5, Example 4 was repeated except that a higher hydrogen flow rate was used.

EXAMPLE 5

Acetone dimerization was thus performed as in Example 4. The hydrogen flow rate was increased to 12 normal liters per hour. The results are shown in Table 5. With the increase in hydrogen flow rate more methyl isobutyl ketone is formed from mesityl oxide hydrogenation; however, not all of the mesityl oxide formed is converted to methyl isobutyl ketone. This indicates that either higher hydrogen flow rates are desirable under the low pressure conditions of 5 bar used in this run or the pressure needs to be increased above 5 bar while maintaining the hydrogen flow rate of 12 normal liters per hour.

TABLE 5

|  |  | % Selectivity to |  |  | Temperature° C. |  |
|---|---|---|---|---|---|---|
| Time (hrs) | Acetone Conv % | MSO + Isomer | MIBK | Others | Reaction Zone 56 | Reboiler 26 |
| 4 | 4.8 | 56.90 | 30.80 | 9.10 | 120.3 | 127.4 |
| 8 | 5.64 | 48.40 | 29.30 | 15.70 | 122.5 | 128.2 |
| 14 | 17.59 | 44.50 | 37.20 | 16.90 | 122.9 | 133 |

TABLE 5-continued

| Time (hrs) | Acetone Conv % | % Selectivity to | | | Temperature° C. | |
| | | MSO + Isomer | MIBK | Others | Reaction Zone 56 | Reboiler 26 |
| --- | --- | --- | --- | --- | --- | --- |
| 20 | 42.80 | 37.60 | 41.30 | 19.80 | 122.8 | 135.9 |
| 24 | 62.80 | 31.60 | 45.00 | 22.20 | 121.2 | 149.8 |
| 28 | 96.01 | 30.77 | 45.50 | 22.20 | 122.7 | 155.9 |

In Example 6 the pressure was maintained at 5 bars and the hydrogen flow rate increased even further.

EXAMPLE 6

Acetone dimerization was performed as in Example 5. The hydrogen flow rate was increased to 55 normal liters per hour. The results are shown in Table 6. With the increase in hydrogen flow rate more methyl isobutyl ketone is formed from mesityl oxide hydrogenation. It is clear from Table 5 and Table 6 that fewer by-products are formed when the hydrogen flow rate is increased from 12 to 55 normal liters per hour indicating the by-products are formed from the mesityl oxide intermediate.

TABLE 6

| Time (hrs) | Acetone Conv % | % Selectivity to | | | Temperature° C. | |
| | | MSO + Isomer | MIBK | Others | Reaction Zone 56 | Reboiler 26 |
| --- | --- | --- | --- | --- | --- | --- |
| 6 | 9.23 | 37.6 | 54.1 | 7.5 | 122 | 129 |
| 12 | 14.59 | 35.4 | 58.4 | 8.1 | 122 | 131 |
| 18 | 21.11 | 31.2 | 61.3 | 5.8 | 122 | 134 |
| 24 | 48.69 | 29.2 | 64.9 | 5.6 | 121 | 135 |
| 43 | 84.69 | 27.1 | 67.4 | 5.5 | 123 | 148 |
| 48 | 92.82 | 26.7 | 67.6 | 5.4 | 122 | 156 |

The invention claimed is:

1. A process for producing methyl isobutyl ketone, which process comprises
   introducing acetone and hydrogen into a treatment zone;
   subjecting the acetone to catalytic distillation in the treatment zone in the presence of the hydrogen, to convert at least some of the acetone to methyl isobutyl ketone; and
   withdrawing methyl isobutyl ketone from the treatment zone.

2. A process according to claim 1 wherein the treatment zone comprises (i) at least one reaction zone in which a dimerization/dehydration reaction of the acetone to convert it to mesityl oxide, and a hydrogenation reaction to convert the mesityl oxide to the methyl isobutyl ketone take place in the presence of a catalyst, and (ii) at least one distillation zone adjacent the reaction zone in which distillation of the reaction products from the reaction zone and/or unreacted reactants takes place.

3. A process according to claim 2 wherein the catalyst is bifunctional so that it promotes or catalysts the dimerization/dehydration reaction and the hydrogenation reaction.

4. A process according to claim 3 wherein the catalyst comprises (i) an ion exchange resin, a zeolite or alumina for promoting or catalyzing the dimerization/dehydration reaction, and (ii) nickel, palladium or copper for promoting or catalyzing the hydrogenation reaction.

5. A process according to any one of claims 2 to 4, wherein the treatment zone is provided by a column, with the catalyst being in particulate form, and being provided in the form of a packed bed located in the reaction zone, above the point or level at which the introduction of the acetone into the column is effected, and with packed distillation media being provided in the column below and/or above the catalyst bed in the distillation zone(s).

6. A process according to claim 5 wherein the temperature and pressure inside the column are such that the acetone is at its boiling point at the column pressure.

7. A process according to claim 5 wherein the introduction of the hydrogen into the column is at a lower level than that of the acetone but below the catalyst bed.

8. A process according to claim 7 which includes allowing the methyl isobutyl ketone and any other by-products that are formed and condensed acetone to pass to the bottom of the reaction zone; reboiling these components in a reboiling stage; and removing the methyl isobutyl ketone and any said other by-products, which have higher boiling points than acetone and are thus not significantly vaporized by the reboiling as a product fraction or stream.

9. A process according to claim 8 which includes withdrawing any unreacted vaporized acetone from the top of the column; condensing the withdrawn vaporized acetone; and returning the condensed acetone as a reflux to the column, at or above the catalyst bed.

10. A process according to claim 8 wherein the process is a continuous process with the introduction of the acetone being into the bottom of the column immediately above the reboiling stage and with the product fraction or stream being withdrawn continuously from the reboiling stage.

11. A process according to claim 8 wherein the process is a batch process with the introduction of the acetone initially being effected into the reboiling stage and the process being terminated when a particular product specification is achieved in the reboiling stage, whereafter the methyl isobutyl ketone-containing product fraction is withdrawn from the reboiling stage.

12. A process for the production of methyl isobutyl ketone comprising the steps of:
   (a) charging acetone and hydrogen to a catalytic distillation column containing a bifunctional catalyst in a reaction zone;
   (b) concurrently in said reaction zone;
      (i) reacting said acetone and hydrogen to produce a reaction mixture containing unreacted acetone, unreacted hydrogen and reaction product containing methyl isobutyl ketone, and
      (ii) separating the reaction product containing methyl isobutyl ketone from the unreacted acetone and unreacted hydrogen;
   (c) withdrawing the reaction product from said catalytic distillation column at a point below said reaction zone; and
   (d) withdrawing unreacted acetone and unreacted hydrogen from said catalytic distillation column at a point above said reaction zone.

13. The process according to claim 12 wherein said bifunctional catalyst comprises an acidic ion exchange resin and a Group VII or IB hydrogenation metal.

14. The process according to claim 13 wherein said catalyst comprises 0.05 wt. % Pd on cation exchange resin.

15. The process according to claim 12 wherein said bifunctional catalyst comprises a zeolite combined with a Group VIII or IB hydrogenation metal.

16. The process according to claim 12 wherein said unreacted acetone and unreacted hydrogen are withdrawn from said catalytic distillation column as overheads.

17. The process according to claim 16 wherein said overheads are cooled to condense said unreacted acetone and substantially all of said acetone is returned to said catalytic distillation column as overheads.

18. The process according to claim 12 wherein said reaction product is withdrawn from said catalytic distillation column as bottoms.

19. The process according to claim 12 wherein said reaction product comprises methyl isobutyl ketone and mesityl oxide.

20. The process according to claim 19 wherein said reaction product is further treated to separate said methyl isobutyl ketone from said mesityl oxide.

21. A process for the production of methyl isobutyl ketone comprising the steps of:

(a) charging acetone and hydrogen to a catalytic distillation column containing a catalyst comprising 0.05 wt. % Pd on ion exchange resin in a reaction zone;

(b) concurrently in said reaction zone;
  (i) reacting said acetone and hydrogen to produce a reaction mixture containing unreacted acetone, unreacted hydrogen and reaction product containing methyl isobutyl ketone and mesityl oxide;
  (ii) separating the reaction product containing methyl isobutyl ketone and mesityl oxide from the unreacted acetone and unreacted hydrogen;

(c) withdrawing the reaction product from said catalytic distillation column as bottoms;

(d) withdrawing unreacted acetone and unreacted hydrogen from said catalytic distillation column as overheads;

(e) cooling said overheads to condense said unreacted acetone;

(f) returning substantially all of said acetone to said catalytic distillation column as reflux; and (g) separating said methyl isobutyl ketone from the remainder of said reaction product.

22. A process according to claim 6 wherein the introduction of the hydrogen into the column is at a lower level than that of the acetone but below the catalyst bed.

23. A process according to claim 22 which includes allowing the methyl isobutyl ketone and any other by-products that are formed and condensed acetone to pass to the bottom of the reaction zone; reboiling these components in a reboiling stage; and removing the methyl isobutyl ketone and any said other by-products, which have higher boiling points than acetone and are thus not significantly vaporized by the reboiling as a product fraction or stream.

24. A process according to claim 23 which includes withdrawing any unreacted vaporized acetone from the top of the column; condensing the withdrawn vaporized acetone; and returning the condensed acetone as a reflux to the column, at or above the catalyst bed.

25. A process according to claim 24 wherein the process is a continuous process with the introduction of the acetone being into the bottom of the column immediately above the reboiling stage and with the product fraction or stream being withdrawn continuously from the reboiling stage.

26. A process according to claim 24 wherein the process is a batch process with the introduction of the acetone initially being effected into the reboiling stage and the process being terminated when a particular product specification is achieved in the reboiling stage, whereafter the methyl isobutyl ketone-containing product fraction is withdrawn from the reboiling stage.

* * * * *